US005684050A

United States Patent [19]

Clark, Jr. et al.

[11] Patent Number: 5,684,050
[45] Date of Patent: *Nov. 4, 1997

[54] STABLE EMULSIONS OF HIGHLY FLUORINATED ORGANIC COMPOUNDS

[75] Inventors: Leland C. Clark, Jr., Cincinnati, Ohio; Robert Francis Shaw, San Francisco, Calif.

[73] Assignee: HemaGen/PFC, St. Louis, Mo.

[*] Notice: The term of this patent shall not extend beyond the expiration date of Pat. No. 5,514,720.

[21] Appl. No.: 441,531

[22] Filed: May 15, 1995

Related U.S. Application Data

[63] Continuation-in-part of Ser. No. 464,647, Jan. 11, 1990, abandoned, and a division of Ser. No. 178,860, Apr. 7, 1988, which is a continuation of Ser. No. 883,713, Jul. 9, 1986, abandoned, said Ser. No. 464,647, is a continuation of Ser. No. 346,340, Apr. 28, 1989, abandoned, which is a continuation of Ser. No. 235,837, Aug. 18, 1988, abandoned, which is a continuation of Ser. No. 822,291, Jan. 24, 1986, abandoned.

[51] Int. Cl.$^6$ .......................... A61K 31/03; A61K 31/02; A61K 31/035; A61K 31/025
[52] U.S. Cl. .......................... 514/749; 514/743; 514/744; 514/756; 514/759; 514/761
[58] Field of Search .................. 514/761, 759, 514/756, 744, 749, 743

[56] References Cited

U.S. PATENT DOCUMENTS

| | | | |
|---|---|---|---|
| 2,055,083 | 9/1936 | Klein et al. | 167/82 |
| 3,778,381 | 12/1973 | Rosano et al. | 252/311 |
| 3,793,450 | 2/1974 | Schnell | 424/195 |
| 3,823,091 | 7/1974 | Samejima et al. | 252/312 |
| 3,911,138 | 10/1975 | Clark, Jr. | 424/352 |
| 3,914,294 | 10/1975 | Bernstein et al. | 424/5 |
| 3,942,527 | 3/1976 | Li | 128/214 R |
| 3,958,014 | 5/1976 | Watanabe et al. | 424/366 |
| 3,962,439 | 6/1976 | Yokoyama et al. | 514/382 |
| 3,975,512 | 8/1976 | Long, Jr. | 424/5 |
| 3,989,843 | 11/1976 | Chabert et al. | 424/325 |
| 3,993,581 | 11/1976 | Yokoyama et al. | 252/312 |
| 4,073,879 | 2/1978 | Long, Jr. | 424/358 |
| 4,073,943 | 2/1978 | Wretlind et al. | 424/358 |
| 4,105,798 | 8/1978 | Moore et al. | 424/352 |
| 4,110,474 | 8/1978 | Lagow et al. | 424/350 |
| 4,186,253 | 1/1980 | Yokoyama et al. | 435/240 |
| 4,252,827 | 2/1981 | Yokoyama et al. | 424/366 |
| 4,285,928 | 8/1981 | Wada et al. | 424/5 |
| 4,325,972 | 4/1982 | Geyer et al. | 424/325 |
| 4,343,797 | 8/1982 | Exanow | 424/199 |
| 4,366,169 | 12/1982 | White | 424/285 |
| 4,395,393 | 7/1983 | Schmolka | 424/78 |
| 4,397,870 | 8/1983 | Sloviter | 424/325 |
| 4,423,077 | 12/1983 | Sloviter et al. | 514/832 |
| 4,425,347 | 1/1984 | Yokoyama et al. | 424/256 |
| 4,443,480 | 4/1984 | Clark, Jr. | 424/352 |
| 4,446,154 | 5/1984 | Osterholm | 424/350 |
| 4,452,818 | 6/1984 | Haidt | 424/352 |
| 4,461,717 | 7/1984 | Moore | 242/312 |
| 4,486,417 | 12/1984 | Sugimoto et al. | 424/180 |
| 4,497,829 | 2/1985 | Sloviter | 514/672 |
| 4,526,969 | 7/1985 | Yokoyama et al. | 546/164 |
| 4,534,978 | 8/1985 | Yokoyama et al. | 514/429 |
| 4,542,147 | 9/1985 | Yokoyama et al. | 514/411 |
| 4,562,183 | 12/1985 | Tatlow et al. | 514/214 |
| 4,569,784 | 2/1986 | Moore | 252/315.1 |
| 4,591,599 | 5/1986 | Yokoyama et al. | 514/413 |
| 4,599,343 | 7/1986 | Yokoyama et al. | 514/299 |
| 4,657,532 | 4/1987 | Osterholm | 604/24 |
| 4,866,096 | 9/1989 | Schweighardt | 514/756 |
| 4,895,876 | 1/1990 | Schwighardt et al. | 514/747 |
| 5,171,755 | 12/1992 | Kaufman et al. | 514/749 |
| 5,514,720 | 5/1996 | Clark, Jr. et al. | 514/749 |
| 5,536,753 | 7/1996 | Clark, Jr. | 514/749 |

FOREIGN PATENT DOCUMENTS

| | | |
|---|---|---|
| 0051526 | 5/1982 | European Pat. Off. |
| 0080716 | 6/1983 | European Pat. Off. |
| 0089232 | 9/1983 | European Pat. Off. |
| 0144434 | 6/1985 | European Pat. Off. |
| 0158996 | 10/1985 | European Pat. Off. |
| 0220152 | 4/1987 | European Pat. Off. |
| 0220153 | 4/1987 | European Pat. Off. |
| 2494992 | 6/1982 | France |
| 51-26213 | 3/1976 | Japan |
| 58-32829 | 2/1983 | Japan |
| 8403624 | 9/1984 | WIPO |
| 8600810 | 2/1986 | WIPO |

OTHER PUBLICATIONS

K. Yokoyama et al. "A Perfluorochemical Emulsion as an Oxygen Carrier", Artificial Organs, 8, pp. 34–40, 1984.

S. Ljungberg et al. "Intravenous Injection of Lipid Soluble Drugs", Acta Pharm. Suecica, 7, pp. 435–440, 1970.

H. Ohyanagi et al. "Development and Clinical Application of Perfluorochemical Artificial Blood", Int. J. Artificial Organs, 9, pp. 363–368, 1986.

A. Wretlind, "Current Status of Intralipid and Other Fat Emulsions", in Fat Emulsions Parenter, Nutr., H.C. Meng et al., eds., American Medical Association, Chicago, IL, pp. 109–122, 1976.

A. Wretlind, "Development of Fat Emulsions", J. Parenter. Enteral Nutr., 5, pp. 2301–2335, 1981.

R. Jeppsson et al., "The Influence of Emulsifying Agents and of Lipid Soluble Drugs on the Fractional Removal Rate of Lipid Emulsions from the Blood Stream of the Rabbit", Acta Pharmacol. et Toxicol., 37, pp. 134–144, 1975.

R. Jeppsson et al. "The Ultrastructure of Lipid Particles in Emulsions Prepared with Various Emulsifiers", Aust. J. Exp. Biol. Med. Sci., 52, pp. 697–702, 1974.

(List continued on next page.)

*Primary Examiner*—Raymond Henley, III
*Attorney, Agent, or Firm*—Fish & Neave; James F. Haley, Jr.; Andrew S. Marks

[57] ABSTRACT

Stable emulsions of highly fluorinated organic compounds for use as oxygen transport agents, "artificial bloods" or red blood cell substitutes and as contrast agents for biological imaging. The emulsions comprise a highly fluorinated organic compound, an oil that is not substantially surface active and not significantly soluble in water, a surfactant and water.

26 Claims, No Drawings

OTHER PUBLICATIONS

R. Jeppsson et al. "Compatability of Parenteral Nutrition Solutions when mixed in a Plastic Bag", Clin. Nutr. 2, pp. 149–158, 1974.

R. Jeppsson et al. "Particle Size Distribution of a Fluorochemical Emulsion", in Proceedings of the HS Symposium on Perfluorochemicals in Medicine and Biology, Huddinge, Sweden, Apr. 28–29, V. Novakova et al., eds., pp. 108–113, 1977.

L.C. Clark et al. "Emulsions of Perfluorinated Solvents for Intravascular Gas Transport", Fed.Proc., 34, pp. 1468–1477, 1975.

R. Jeppsson, "Comparison of Pharmacological Effects of Some Local Anaesthetic Agents when using Water and Llpid Emulsion as Injection Vehicles", Acta Pharmacol. et Toxicol., 36 pp. 299–311, 1975.

R. Jeppsson, "Parabolic Relationship between Lipophilicity and Biological Activity of Aliphatic Hydrocarbons Ethers and Ketones after Intravenous Injections of Emulsion Formulations into Mice", Acta Pharmacol. et Toxicol., 37, pp. 56–64, 1975.

R. Jeppsson, et al., "Anticonvulsant Activity in Mice of Diazepam in an Emulsion Formulation for Intravenous Administration", Acta Pharmacol. et Toxicol., 36 pp. 312–320, 1975.

STABLE EMULSIONS OF HIGHLY FLUORINATED ORGANIC COMPOUNDS

This application is a division of application Ser. No. 07/178,860, filed Apr. 7, 1988, abandoned, which is a continuation of application Ser. No. 06/883,713, filed Jul. 9, 1986, now abandoned, and a continuation-in-part of application Ser. No. 07/464,647, filed Jan. 11, 1990 now abandoned. The Ser. No. 07/464,647 application, which is a further continuation of application Ser. No. 07/346,340, filed Apr. 28, 1989, now abandoned, which is a continuation of application Ser. No. 07/235,837, filed Aug. 18, 1988, now abandoned, which is a continuation of application Ser. No. 06/822,291, filed Jan. 24, 1986, now abandoned.

TECHNICAL FIELD OF INVENTION

This invention relates to stable emulsions of highly fluorinated organic compounds and to processes of making and using them. More particularly, this invention relates to novel emulsions, stable even at room temperature, that comprise an oil, that is not substantially surface active and not significantly soluble in water, water, a surfactant and a highly fluorinated organic compound. Such emulsions are especially useful in compositions for use as oxygen transport agents, "artificial bloods" or red blood cell substitutes and as contrast agents for biological imaging.

BACKGROUND OF THE INVENTION

Highly fluorinated organic compounds are well known to be chemically and pharmaceutically inert and to be capable of dissolving and transporting large amounts of oxygen. These properties make them potentially useful as oxygen transport agents, "artificial bloods" or red blood cell substitutes and as contrast agents for various imaging modalities, such as nuclear magnetic resonance, ultrasound, and x-ray. However, neat fluorocarbon liquids cannot be injected into the blood stream, because their hydrophobic character makes them immiscible in the blood and, as a result when they are transported into small blood vessels they may cause vascular obstruction and death. As a consequence, for medical uses that require intravascular injection, highly fluorinated organic compounds must be dispersed as physiologically acceptable emulsions. See, e.g., L. C. Clark, Jr. et al., "Emulsions Of Perfluorinated Solvents For Intravascular Gas Transport", *Fed. Proc.*, 34(6), pp. 1468–77 (1975); K. Yokoyama et al., "A perfluorochemical Emulsion As An Oxygen Carrier", *Artif. Organs* (Cleve), 8(1), pp. 34–40 (1984); and U.S. Pat. Nos. 4,110,474 and 4,187,252.

To date, however, the medical usefulness of such emulsions of highly fluorinated organic compounds as "artificial bloods" or blood substitutes, oxygen transport agents or contrast agents for biological imaging has not been as successful as hoped. This results from the fact that in practice it has not been previously possible to make emulsions that are both stable and incorporate the relatively large amounts of highly fluorinated organic compounds that are required in clinical practice where the total volume of emulsion that can be administered is limited, e.g., as "artificial bloods". Moreover, it has not been previously possible to make such emulsions using highly fluorinated organic compounds that are excreted from the body within a clinically acceptable time period (see U.S. Pat. No. 3,911,138). Finally, even those, admittedly less than therapeutically acceptable, compositions that have been available to date are difficult to sterilize because of their instability at high temperature.

Various attempts have been made to solve these problems and to prepare stable emulsions containing high concentrations of clinically suitable highly fluorinated organic compounds. None has been successful. For example, a variety of fluorocarbons and combinations of them have been used in preparing the emulsions in hopes of improving their stability. None has produced a medically effective and commercially acceptable emulsion that is stable at room temperature. For example, the only fluorocarbon emulsion to reach clinical testing as an "artificial blood", "Fluosol DA 20%", is about a 12% by volume emulsion of two fluorocarbons—perfluorodecalin and perfluorotripropylamine—in a mixture of two surfactants—yolk phospholipid and Pluronic F-68. It is not stable in the liquid state and must be stored frozen (Yokoyama et al., supra). Furthermore, the required presence of the perfluorotripropylamine in this emulsion, to help "stabilize" it, disadvantages the emulsion's medical usefulness because the half-life of the perfluorotripropylamine in the liver and other body tissues is longer than desirable (see, e.g., K. Yokoyama et al., supra). Finally, because this emulsion contains only about 12% fluorocarbon by volume, it is much less therapeutically effective than desired because of its low oxygen content capacity (see, e.g., "Fluosol-DA As A Red Cell Substitute In Acute Anemia", *N. E. Jour. Med.*, 314, pp. 1653–66 (1986).

Emulsions of other perfluorocarbons have likewise not been very effective in avoiding these instability and oxygen capacity problems. For example, an emulsion of perfluoro-4-methyloctahydroquinolidizine (FMOQ) in two surfactants—Pluronic F-68 and yolk phospholipid—must be stored at 4° C. (K. Yokoyama et al., supra).

Various surfactants have also been investigated in the hope that some would produce useful, stable emulsions of highly fluorinated organic compounds for use as oxygen transport agents and "artificial bloods". Again, these attempts have failed. For example, fluorocarbon emulsions containing a hydrogenated phospholipid, a nonionic polymeric surfactant and a surfactant selected from 6–22 C fatty acids, their salts and monoglycerides must also be stored at 4° C. See, e.g., Japanese patent application 59,067,229, U.S. Pat. No. 4,252,827 and Germany Offen. DE 2630506.

Therefore, the medical and non-medical uses of highly fluorinated organic compounds as effective oxygen transport agents, "artificial bloods" or red blood cell substitutes, and contrast agents for biological imaging is still a long sought and important goal.

SUMMARY OF THE INVENTION

This invention solves the problems referred to above. This invention provides novel emulsions of highly fluorinated organic compounds for use as oxygen transport agents, "artificial bloods" or red blood cell substitutes, and as contrast agents for various biological imaging modalities. This invention also provides emulsions that are stable even when they contain the higher levels of highly fluorinated organic compounds that are required in emulsions for use as blood substitutes because of the high oxygen content capacity required in that application. This invention also provides stable emulsions that employ only those fluorocarbons that display acceptably rapid excretion times from the liver and other body tissues. Finally, this invention provides emulsions that are easily sterilized.

The emulsions of this invention comprise at least one highly fluorinated organic compound; an oil that is not substantially surface active and not significantly soluble in water; a surfactant and water.

This invention also includes methods of making these emulsions and methods and compositions of using them as oxygen transport agents, "artificial bloods" or red blood cell substitutes, and contrast agents for biological imaging.

DETAILED DESCRIPTION OF THE INVENTION

The emulsions of this invention comprise at least one highly fluorinated organic compound; an oil that is not substantially surface active and not significantly soluble in water; a surfactant and water.

The preferred emulsions of this invention are stable at room temperature for long periods of time. They exhibit substantially no phase separation and substantially no change in particle or droplet size distribution during storage. Moreover, they permit the use of highly fluorinated organic compounds that exhibit acceptably rapid excretion times from the liver and other body tissues. And, they permit the use of the high concentrations of fluorocarbons thereby producing the high oxygen content capacity emulsions required for use of the emulsions of this invention as therapeutically effective blood substitutes. Finally, because of their stability, the emulsions of this invention may be sterilized by heating them to high temperature, for example, 115° C. for 15 min. It is one very surprising aspect of this invention that even such harsh conditions do not cause phase separation of the emulsions of this invention. As a result of these novel and unexpected properties, the emulsions of this invention solve the long standing problems of prior fluorocarbon-containing compositions and make these highly fluorinated organic compounds available for the first time in commercially useful forms for use as oxygen transport agents, "artificial bloods" or red blood cell substitutes and as contrast agents for biological imaging.

While not wishing to be bound by theory, we believe that the emulsions of this invention may have the highly fluorinated organic compound dispersed in oil and that oil-fluorocarbon combination emulsified in the water and surfactant. However, other possible phases and interfaces are also within the scope and intent of this invention.

Among the highly fluorinated organic compounds that are useful in the emulsions and processes of this invention are those previously said to be useful as oxygen transport agents, "artificial bloods" or red blood cell substitutes, and contrast agents for biological imaging. These include, for example, perfluorocarbons, partially fluorinated hydrocarbons and derivatives and mixtures of them. For example, among the fluoro-containing compounds useful in the emulsions of this invention are 9–18C perfluorohydrocarbons, e.g., perfluorodecalin, perfluoro-trimethyl-bicyclo [3.3.1] nonane and perfluoro-2,2,4,4-tetramethylpentane, 9–12C perfluoroamines, e.g., perfluorotripropylamine, perfluorotributylamine, perfluorodimethyladamantane, perfluoro-1-aza-tricylic amines, bromo- or iodo-substituted fluorocarbons, and F-4-methyloctahydroquinolidizine. Such compounds are described, for example, in U.S. Pat. Nos. 3,962,439, 3,493,581, 4,110,474, 4,186,253, 4,187,252, 4,252,827, 4,423,077, 4,443,480, 4,534,978 and 4,542,147, European patent applications 80710 and 158,996, British patent specification 1,549,038 and German Offen. 2,650, 586. Of course, it should be understood that mixtures of any of these highly fluorinated organic compounds may also be used in the emulsions and processes of this invention.

Preferably, the emulsions of this invention contain one or more of a perfluorocarbon and most preferably a fluorocarbon selected from the group consisting of perfluorodecalin, perfluorodimethyladamantane, perfluorooctylbromide, perfluoro-4-methyloctahydroquinolidizine, perfluoro-N-methyl-decahydroquinoline, F-methyl-1-oxa-decalin, perfluoro-bicyclo[5.3.0]decane, perfluorooctahydroquinolidizine, perfluoro-5,6-dihydro-5-decene, and perfluoro-4,5-dihydro-4-octene. For use as a contrast agent for biological imaging perfluorooctylbromide is one of the preferred highly fluorinated organic compounds according to this invention.

While the highly fluorinated organic compounds or mixture of such compounds may comprise up to about 75% (by volume) of the emulsions of this invention. Preferably, the emulsions of this invention comprise from 10% to about 70% (by volume) of the fluorocarbon. When the emulsions are to be used as "artificial bloods" or red blood cell substitutes, the fluoro-containing compounds are preferably present in as high a volume concentration as possible. However, 40% (by volume) is often preferred because that concentration matches the approximate oxygen content capacity of whole blood.

Among the not substantially surface active and not significantly water soluble oils that are useful in the emulsions and processes of this invention are liquid fatty oils, hydrocarbons, waxes, such as monoesters of a fatty acid and a monohydroxide alcohol, long chain ethers, diglycerides, silicone oils and nitriles. These include, for example, palmitoyl oleate, octyl nitrile, dodecyl nitrile, soy oil, safflower oil, hexadecane, diglycerides having a $C_{12-18}$ carbon chain and one unsaturation, and mineral oil. As with the fluoro-containing component, these oils also may be used singly or in various combinations in the emulsions and processes of this invention. When our emulsions are to be used medically, the oil or combination of oils must, of course, be physiologically acceptable. For example, when our emulsions are to be used as "artificial bloods", we preferably use physiologically acceptable liquid fatty oils.

The amount of oil, or oils, present in the emulsions of this invention may vary over a wide range of concentrations. It depends on the concentration and properties of the other components of the emulsion, being principally dependent on the characteristics of the fluorocarbon component of the emulsion. The actual oil concentration to produce an acceptable emulsion for any given set of components is easily determined as taught by this invention using the simple techniques of preparing and testing the stability of emulsions at various oil concentrations. Within this teaching, we typically employ between about 10 and 30% (by weight of the remaining non-fluorocarbon volume of the emulsion) of oil or a mixture of oils. Preferably, we employ between about 15 and 20% by weight.

Among the surfactants useful in the emulsions of this invention are any of the known anionic, cationic, nonionic and zwitterionic surfactants. These include, for example, anionic surfactants, such as alkyl or aryl sulfates, sulfonates, carboxylates or phosphates, cationic surfactants such as mono-, di-, tri-, and tetraalkyl or aryl ammonium salts, nonionic surfactants, such as alkyl or aryl compounds, whose hydrophilic part consists of polyoxyethylene chains, sugar molecules, polyalcohol derivatives or other hydrophilic groups and zwitter-ionic surfactants that may be combinations of the above anionic or cationic groups, and whose hydrophobic part consists of any other polymer, such as polyisobutylene or polypropylene oxides. Again, combinations of these surfactants may, of course, be used in the emulsions of this invention. In addition, mixtures of compounds, one or more of which are not surfactants, but which compounds when combined act as surfactants may also be usefully employed as the surfactant component of the emulsions of this invention.

Again, when the emulsions of this invention are to be used in "artificial bloods" or red blood cell substitutes, the surfactant, or combinations of them, must be physiologically acceptable. For example, in "artificial bloods" we prefer nonionic surfactants. Preferably, the surfactants used in the emulsions of this invention are one or more of the following: egg phosphatides, lecithin, and alkyl salts of oleic acid, such as sodium oleate.

While the amount of a particular surfactant used in the emulsions of this invention depends on the amounts and properties of the other components of the emulsion, typically we employ about 0.5 to 7% (by weight of the non-fluorocarbon volume) of surfactant. More preferably, we use about 1–2% (by weight).

In addition to the highly fluorinated organic compounds, oils, surfactants and water, the emulsions of this invention may also contain other components conventionally used in "artificial bloods" or blood substitutes, oxygen transport agents or contrast agents for biological imaging. For example, when used as a blood substitute, an emulsion according to this invention should contain an isotonic agent, typically glycerol, to adjust the osmotic pressure of the emulsion to about that of blood. Typically we use about 2.5% (by weight of the non-fluorocarbon volume) of glycerol. However, other amounts and other osmotic pressure controlling agents, e.g., Tyrode solution, could as well be used. The emulsions of this invention may also include other components, such as oncotic agents, e.g., dextran or HES, and antioxidants.

The emulsions of this invention may be prepared using any order of mixing the four main components of our emulsions—highly fluorinated organic compound, oil, surfactant and water. However, for an optimal emulsion we prefer to mix the fluorocarbon first with the oil in the presence of a combination of all or part of the surfactant and some water. We then prepare the final emulsion by emulsifying this first emulsion in the remaining water and any remaining surfactant.

The mixing and emulsification of our components may be done using any of the conventional mixers and emulsifiers. For example, we may employ Fisher brand touch mixers and Microfluidizers. We may also, if desired, reduce the average size of the droplets or particles in our emulsions by conventional grinding.

The following non-limiting examples illustrate various embodiments of this invention.

EXAMPLE 1

In this example, we prepared two emulsions in the same manner to compare their stabilities. The first emulsion was a conventional composition comprising 40% by volume perfluorodecalin and 60% by volume of a mixture of water (96.3% by weight), lecithin (1.2% by weight), glycerol (2.5% by weight) and sodium hydroxide to pH 8. The second emulsion was prepared according to this invention. It had the following composition: 40% by volume perfluorodecalin and 60% by volume of a mixture of water (78.8% by weight), lecithin (1.2% by weight), glycerol (2.5% by weight), soy oil (17.5% by weight) and sodium hydroxide to pH 8. The two emulsions were prepared by mixing their components together in a Fisher brand touch mixer and then running them through a Microfluidizer for 30 min at 60 psi.

The first emulsion had a smaller average droplet size by optical microscopy than the second emulsion. It also had a higher concentration of water and thus less dispersed phase than the second emulsion. Accordingly, on those bases alone, we would have expected the first emulsion to be more stable than the second emulsion. However, the first "emulsion" was very unstable and exhibited phase separation at room temperature within 24 hours. The second emulsion (that prepared in accordance with this invention), while having a larger average droplet or particle size and more dispersed phase, was surprisingly very stable and showed substantially no phase separation and substantially no change in droplet or particle size distribution during 4 weeks storage at room temperature.

This comparison plainly demonstrates that the emulsions of this invention are different in kind from former compositions of highly fluorinated organic compounds. Not only are our emulsions far more stable, they are surprisingly more stable even with larger average particle or droplet size and more dispersed phase.

EXAMPLE 2

We prepared an emulsion containing 40% by volume perfluorodecalin and 60% by volume of a first emulsion containing safflower oil (10% by weight), soybean oil (10% by weight), lecithin (1.2% by weight), glycerol (2.5% by weight), water (76.3% by weight) and sodium hydroxide to pH 8.3. We prepared the final emulsion by combining 20 ml perfluorodecalin and 30 ml of the first emulsion and mixing the combination in a Fisher touch-mixer for 20 min. We then ran the resulting emulsion through a Microfluidizer for 1 hour at 60 psi.

The resulting homogenized emulsion was still stable after 4 weeks at room temperature, as demonstrated by optical microscopy which indicated that there had been substantially no change in particle or droplet size distribution and substantially no phase separation.

EXAMPLE 3

Using the substantially same process as described in Example 2, we prepared an emulsion containing 40% by volume perfluorodecalin and 60% by volume of a first emulsion containing safflower oil (10% by weight), soybean oil (10% by weight), lecithin (2.0% by weight), glycerol (2.5% by weight), water (75.5% by weight) and sodium hydroxide to pH 8.3. As before, the resulting emulsion was still stable after 4 weeks at room temperature.

EXAMPLE 4

We prepared an emulsion containing 40% by volume perfluorodecalin and 60% by volume of a first emulsion containing safflower oil (10% by weight), soybean oil (10% by weight), lecithin (2.0% by weight), glycerol (2.5% by weight), XMO-20 (see, e.g., U.S. Pat. No. 4,443,480) (0.1% by weight), water (75.4% by weight) and sodium hydroxide to pH 8.3. We prepared the final emulsion by combining 20 ml perfluorodecalin and 30 ml of the first emulsion and mixing the combination in a Fisher touch mixer until the lecithin and XMO-20 were completely dissolved. We then ran the emulsion through a Microfluidizer for 30 min at 60 psi. The resulting emulsion was still stable after 4 weeks at room temperature.

EXAMPLE 5

We prepared an emulsion containing 40% by volume perfluorodecalin and 60% by volume of a first emulsion containing safflower oil (10% by weight), soybean oil (10% by weight), lecithin (1.2% by weight), glycerol (2.5% by weight), oleic acid (0.8% by weight), water (75.5% by weight) and sodium hydroxide to pH 8.3. We prepared the final emulsion by mixing 20 ml perfluorodecalin and 30 ml of the first emulsion in a Fisher touch mixer for 10 min and running the resulting emulsion through a Microfluidizer for 45 min. The resulting emulsion was still stable after 4 weeks at room temperature.

EXAMPLE 6

We added lecithin to a final concentration of 2% (by weight) to the final emulsion of Example 5 and mixed it until the lecithin had completely dissolved. The emulsion was then run through a Microfluidizer for 30 min at 60 psi. The resulting emulsion was still stable after 4 weeks at room temperature.

EXAMPLE 7

We prepared an emulsion containing 40% by volume perfluorodecalin and 60% by volume of a mixture containing water (78.8% by weight), lecithin (1.2% by weight), glycerol (2.5% by weight), soybean oil (17.5% by weight) and sodium hydroxide to pH 8.0. We prepared the emulsion by mixing 0.377 g lecithin and 20 ml perfluorodecalin in a Fisher brand touch mixer for 10 min. We then added 5.4915 g soybean oil and mixed again for 10 min and added 0.7945 g glycerol and mixed again for 10 min. Finally, we added 24.721 g water stepwise with mixing. We made this addition by first adding 12.36 g of water to the mixture to disperse the fluorocarbon-oil-lecithin mixture and emulsified the resulting dispersion in a Microfluidizer for 30 min at 60 psi. We then emptied the emulsion from the Microfluidizer and poured the remaining water into the Microfluidizer. After adding the previously prepared emulsion dropwise to the water, we ran the resulting mixture through the Microfluidizer for 30 min at 60 psi and adjusted the pH to 8.0 with sodium hydroxide. We then again ran the emulsion through a Microfluidizer for 30 min at 60 psi. The final emulsion was still stable after 4 weeks at room temperature.

EXAMPLE 8

We prepared an emulsion containing 40% by volume perfluorodecalin and 60% by volume of a mixture containing water (78.8% by weight), lecithin (1.2% by weight), glycerol (2.5% by weight), hexadecane (17.5% by weight) and sodium hydroxide to pH 8.0. We used substantially the same method described in Example 7. The final emulsion was still stable after 4 weeks at room temperature.

EXAMPLE 9

We prepared an emulsion similar to that of Example 8, except that hexadecane was replaced with mineral oil. Again, we used substantially the same method described in Example 7 to prepare the emulsion. The final emulsion was still stable after 4 weeks at room temperature.

EXAMPLE 10

We prepared an emulsion containing 55% by volume perfluorodecalin and 45% by volume of a mixture containing safflower oil (10% by weight), soybean oil (10% by weight), glycerol (2.5% by weight), lecithin (2% by weight) and water (75.5% by weight) and sodium hydroxide to pH 8. To prepare the emulsion we used 18 ml of the oil-containing mixture, 22 ml of perfluorodecalin and 1% (by weight on total) oleic acid. We used the method substantially as described in Example 7. We mixed the final emulsion for 20 min in a Fisher touch mixer and then in a Microfluidizer for 15 cycles at 65 psi. The emulsion was stable at room temperature.

EXAMPLE 11

We prepared an emulsion containing 70% by volume perfluorodecalin and 30% by volume of a mixture containing safflower oil (10% by weight), soybean oil (10% by weight), lecithin (1.2% by weight), glycerol (2.5% by weight), water (76.3% by weight) and sodium hydroxide to pH 8.0. To prepare the final emulsion we used 21 ml perfluorodecalin, 9 ml of the oil-containing mixture, and 0.5% (by weight on total) oleic acid. As in Example 10, we used substantially the same method described in Example 7 to prepare the final emulsion. We then mixed the final emulsion for 20 min in a Fisher touch mixer and then in a Microfluidizer for 15 cycles at 65 psi. The emulsion was stable at room temperature.

EXAMPLE 12

We prepared an emulsion containing 16.5 ml perfluorooctylbromide (55% by volume) and 13.5 ml of the same mixture of other components described in Example 11. We used the same mixing and fluidizing regime described in Examples 10 and 11. The final emulsion was stable at room temperature.

While we have hereinbefore described a number of embodiments of our invention, it should be apparent that other embodiments also exist within our invention. Therefore, it should be understood that the scope of this invention is to be defined by the claims rather than by the specific embodiments which have been presented hereinbefore by way of example.

We claim:

1. A physiologically acceptable emulsion comprising a highly fluorinated organic compound; an oil that is not substantially surface active and not significantly water soluble; a surfactant and water, wherein (a) the highly fluorinated compound is present in the emulsion in an amount between about 15 and 70% by volume;

(b) the oil is present in an amount between about 10 and 30% by weight of the volume of the emulsion excluding the volume of the highly fluorinated organic compound; and (c) the emulsion is stable after heating to at least 115° C. for about 15 minutes.

2. The emulsion according to claim 1, wherein the highly fluorinated organic compound is a perfluorocarbon.

3. The emulsion according to claim 2, wherein said emulsion has a pH before heat-sterilization of about 8.

4. The emulsion according to claim 1, wherein the highly fluorinated organic compound is selected from the group consisting of perfluorodecalin, perfluorodimethyladamantane, perfluorooctylbromide, perfluoro-4-methyl-octahydroquinolidizine, perfluoro-N-methyl-decahydroquinoline, F-methyl-1-oxa-decalin, perfluoro-bicyclo[5.3.0]decane, perfluorooctahydroquinolidizine, perfluoro-5,6-dihydro-5-decene, and perfluoro-4,5-dihydro-4-octene.

5. The emulsion according to claim 4, wherein said emulsion has a pH before heat-sterilization of about 8.

6. The emulsion according to claim 4, wherein the highly fluorinated organic compound is perfluorooctylbromide.

7. The emulsion according to claim 1, wherein said emulsion has a pH before heat-sterilization of about 8.

8. The emulsion according to claim 1, wherein the oil is present in an amount between about 15 and 20% by weight of the volume of the emulsion excluding the volume of the highly fluorinated organic compound.

9. The emulsion according to claim 1, wherein the oil is a physiologically acceptable oil.

10. The emulsion according to claim 9, wherein the oil is selected from the group consisting of liquid fatty oils.

11. The emulsion according to claim 1, wherein the surfactant is present in an amount between about 0.5 and 7% by weight of the non-highly fluorinated organic compound volume of the emulsion.

12. The emulsion according to claim 11, wherein the surfactant is present in an amount between about 1 and 2% by weight of the non-highly fluorinated organic compound volume of the emulsion.

13. The emulsion according to claim 1, wherein the surfactant is a physiologically acceptable surfactant.

14. The emulsion according to claim 13, wherein the surfactant is lecithin.

15. The emulsion according to claim 1 wherein the highly fluorinated organic compound is present in an amount between about 40% and 70% by volume.

16. The emulsion according to claim 15, wherein the oil is selected from the group consisting of liquid fatty oils, diglycerides of $C_{12}$–$C_{18}$ fatty acids having one unsaturation, silicone oils, and mineral oil.

17. The emulsion according to claim 1, further comprising at least one compound of the group consisting of isotonic agents, osmotic pressure controlling agents, serum extending agents and antioxidants.

18. The emulsion according to claim 1, wherein the oil is selected from the group consisting of liquid fatty oils, diglycerides of $C_{12}$–$C_{18}$ fatty acids having one unsaturation, silicone oils, and mineral oil.

19. The emulsion according to claim 1, wherein the oil is selected from the group consisting of triglycerides of fatty acids, diglycerides of $C_{12}$–$C_{18}$ fatty acids having one unsaturation, and mixtures thereof.

20. The emulsion according to claim 19, wherein the oil comprises a triglyceride of fatty acids.

21. A red blood cell substitute comprising an amount of an emulsion according to any one of claims 1–5, 7–13, 14, 15 and 17, said amount being therapeutically effective for oxygen carrying and transport in humans.

22. A contrast agent for biological imaging comprising an amount of an emulsion according to any one of claims 1–5, 7–13, 14, 15 and 17, said amount being clinically effective for imaging by modalities selected from the group consisting of nuclear magnetic resonance, x-ray and ultrasound.

23. A red blood cell substitute comprising an amount of an emulsion according to any one of claims 1–5, 7–13, 15, 14 and 17, said amount being therapeutically effective for oxygen transport and delivery in humans.

24. A physiologically acceptable emulsion comprising
 (a) a highly fluorinated organic compound in an amount between about 15 and 70% by volume;
 (b) an oil that is not substantially surface active and not significantly water soluble in an amount between about 10 and 30% by weight of the non-highly fluorinated organic compound volume;
 (c) a surfactant in an amount between about 0.5 and 7% by weight of the non-highly fluorinated organic compound volume; and
 (d) water, wherein the emulsion is stable after heating to at least 115° C. for about 15 minutes.

25. The emulsion according to claim 24, wherein the oil is selected from the group consisting of triglycerides of fatty acids, diglycerides of $C_{12}$–$C_{18}$ fatty acids having one unsaturation, and mixtures thereof.

26. The emulsion according to claim 25, wherein the oil comprises a triglyceride of fatty acids.

* * * * *